US012667320B2

(12) United States Patent
Petkus et al.

(10) Patent No.: US 12,667,320 B2
(45) Date of Patent: Jun. 30, 2026

(54) METHOD AND APPARATUS FOR EARLY WARNING OF CEREBRAL VASOSPASM AFTER SUBARACHNOID HEMORRHAGE

(71) Applicant: Kaunas University of Technology, Kaunas (LT)

(72) Inventors: Vytautas Petkus, Kaunas (LT); Algis Dziugys, Kauno r. (LT); Arminas Ragauskas, Kaunas (LT); Aidanas Preiksaitis, Vilniaus r. (LT); Edgaras Misiulis, Kaunas (LT); Gediminas Skarbalius, Telsiai (LT); Robertas Navakas, Kaunas (LT); Tomas Iesmantas, Vilnius (LT); Mindaugas Serpytis, Vilnius (LT); Saulius Lukosevicius, Vilnius (LT); Vytenis Ratkunas, Kaunas (LT); Alina Barkauskiene, Vilnius (LT); Indre Lapinskiene, Vilnius (LT); Saulius Rocka, Vilnius (LT); Robertas Alzbutas, Kaunas (LT)

(73) Assignee: Kaunas University of Technology, Kaunas (LT)

( * ) Notice: Subject to any disclaimer, the term of this patent is extended or adjusted under 35 U.S.C. 154(b) by 392 days.

(21) Appl. No.: 18/216,991

(22) Filed: Jun. 30, 2023

(65) Prior Publication Data

US 2025/0000468 A1     Jan. 2, 2025

(51) Int. Cl.
| *A61B 6/50* | (2024.01) |
| *A61B 6/00* | (2024.01) |
| *A61B 6/03* | (2006.01) |
| *G06T 7/11* | (2017.01) |

(52) U.S. Cl.
CPC .............. *A61B 6/501* (2013.01); *A61B 6/032* (2013.01); *A61B 6/504* (2013.01); *A61B 6/5217* (2013.01); *G06T 7/11* (2017.01); *G06T 2207/10081* (2013.01); *G06T 2207/10088* (2013.01); *G06T 2207/30016* (2013.01); *G06T 2207/30101* (2013.01)

(58) Field of Classification Search
CPC ......... A61B 6/501; A61B 6/032; A61B 6/504; A61B 6/5217; A61B 5/02042; G06T 7/11; G06T 2207/10081; G06T 2207/10088; G06T 2211/441; G06T 11/008
See application file for complete search history.

(56) References Cited

FOREIGN PATENT DOCUMENTS

EP        3827841 A1     6/2021

OTHER PUBLICATIONS

Street, James "Predicting vasospasm risk using first presentation aneurysmal subarachnoid hemorrhage volume: A semi-automated CT image segmentation analysis using ITK-SNAP") PLOS One. Jun. 1, 2023 (Year: 2023).*

(Continued)

*Primary Examiner* — Molly Wilburn
(74) *Attorney, Agent, or Firm* — Harris Beach Murtha Cullina PLLC

(57) ABSTRACT

The invention is directed to a method and apparatus for early warning of cerebral vasospasm after subarachnoid hemorrhage using brain imaging equipment to identify blood leakage within the subarachnoid space to detect brain zones with increased risk of cerebral vasospasm.

16 Claims, 16 Drawing Sheets

(56)                 References Cited

OTHER PUBLICATIONS

Sander Connolly E, Jr, Rabinstein Alejandro A, Ricardo Carhuapoma J, Derdeyn Colin P, Jacques D, Higashida Randall T, et al. Guidelines for the management of aneurysmal subarachnoid hemorrhage: Guidelines for healthcare professionals from the American heart association/American stroke association. Stroke. 2012;43:1711-1737.

Ganaw, A. E. A., Tharayil, A. M. , Khair, A. O. M. , Tahseen, S. , Hassan, J. , Abdullah Malmstrom, M. F. , Ahmed, S. M. G. . Aneurysmal Subarachnoid Hemorrhage. In: Shaikh, N., editor. Intensive Care [Internet]. London: IntechOpen; 2017 [cited Oct. 12, 2022]. Available from: https://www.intechopen.com/chapters/55443 doi: 10.5772/intechopen.68630.

Chen T, Carter B. Role of magnesium sulphate in aneurysmal SAH management: A meta-analysis of controlled trial. Asian Journal of the Neurosurgery. 2011;6:1.

William S. Dodd, Dimitri Laurent, Aaron S. Dumont MD , David M. Hasan, Pascal M. Jabbour, Robert M. Starke, Koji Hosaka, Adam J. Polifka, Brian L. Hoh, and Nohra Chalouhi. Pathophysiology of Delayed Cerebral Ischemia After Subarachnoid Hemorrhage: A Review. Journal of the American Heart Association. 2021; 10:e021845

[5] Diringer MN. Management of aneurysmal subarachnoid hemorrhage. Crit Care Med. Feb. 2009;37(2):432-40. doi: 10.1097/CCM.0b013e318195865a. PMID: 19114880; PMCID: PMC2820121. Diringer, Michael N. Management of aneurysmal subarachnoid hemorrhage, Crit Care Med 2009 vol. 37, No. 2.

Park ES, Kim DW, Kang SD. Endovascular Treatment of Symptomatic Vasospasm after Aneurysmal Subarachnoid Hemorrhage: A Three-year Experience. J Cerebrovasc Endovasc Neurosurg. Sep. 2017;19(3):155-161. doi: 10.7461/jcen.2017.19.3.155. Epub Sep. 30, 2017. PMID: 29159148; PMCID: PMC5680078.

Nakagomi, T., Takagi, K., Narita, K., Nagashima, H., Tamura, A. (2001). Cisternal Washing Therapy for the Prevention of Cerebral Vasospasm Following Aneurysmal Subarachnoid Hemorrhage. In: Seiler, R.W., Steiger, HJ. (eds) Cerebral Vasospasm. Acta Neurochirurgica Supplements, vol. 77. Springer, Vienna. https://doi.org/10.1007/978-3-7091-6232-3_34.

Kodama N, Sasaki T, Kawakami M, Sato M, Asari J. Cisternal irrigation therapy with urokinase and ascorbic acid for prevention of vasospasm after aneurysmal subarachnoid hemorrhage. Outcome in 217 patients. Surg Neurol. Feb. 2000; 53(2):110-7; discussion 117-8. doi: 10.1016/s0090-3019(99)00183-4. PMID: 10713187.

Sasaki T, Matsumoto M, Suzuki K, Konno Y, Sakuma J, Kodama N. Prevention of vasospasm-cisternal irrigation therapy with urokinase and ascorbic acid. International Congress Series, vol. 1247, 2002, pp. 611-622, ISSN 0531-5131, https://doi.org/10.1016/S0531-5131(02)01105-6.

M. King Hubbert (1957) Darcy's Law and the Field Equations of the Flow of Underground Fluids, International Association of Scientific Hydrology. Bulletin, 2:1, 23-59, DOI: 10.1080/02626665709493062.

Stephen Whitaker. The transport equations for multi-phase systems. Chemical Engineering Science, vol. 28, Issue 1, 1973, pp. 139-147. https://doi.org/10.1016/0009-2509(73)85094-8.

* cited by examiner

FIG. 1

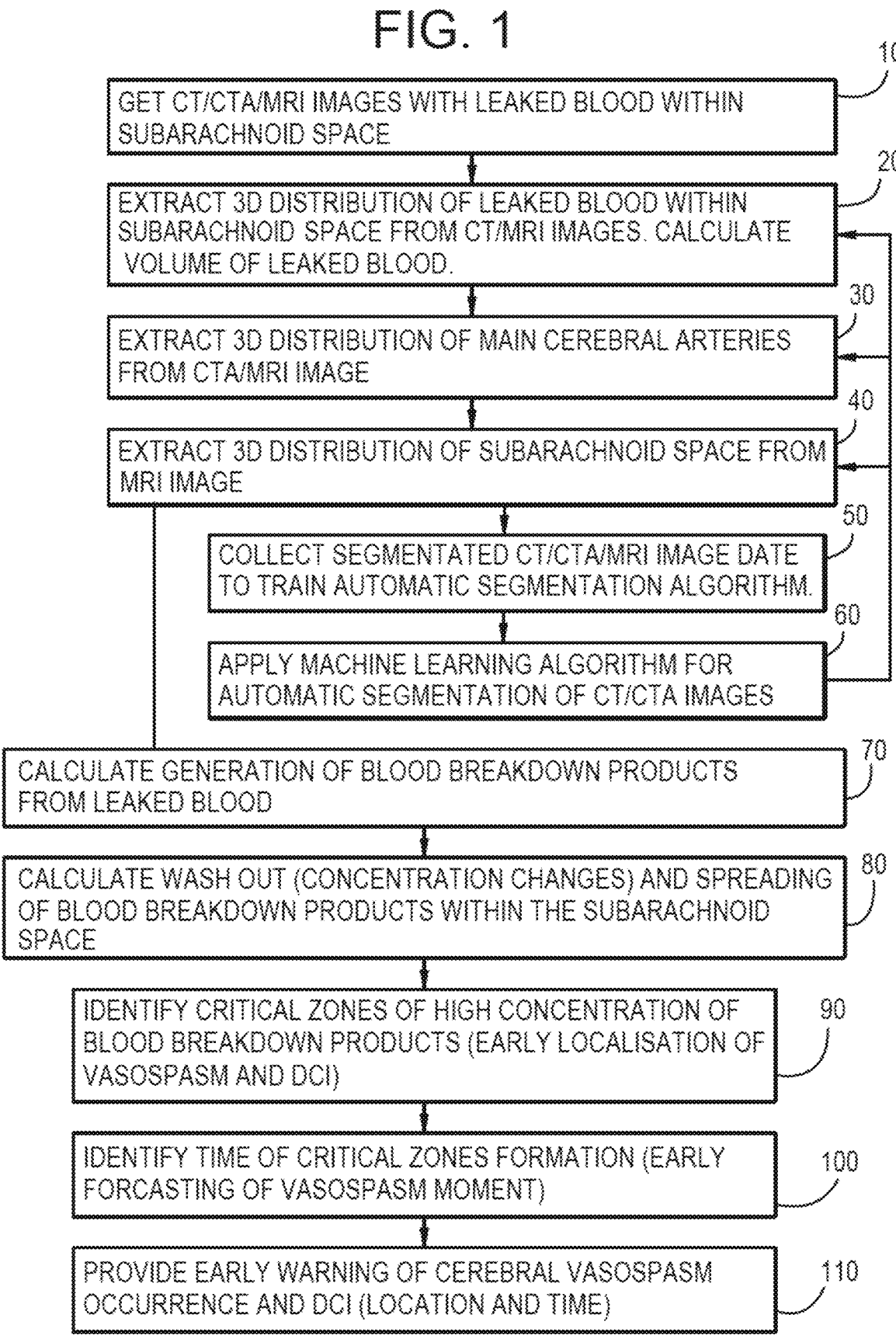

GET CT/CTA/MRI IMAGES WITH LEAKED BLOOD WITHIN SUBARACHNOID SPACE — 10

EXTRACT 3D DISTRIBUTION OF LEAKED BLOOD WITHIN SUBARACHNOID SPACE FROM CT/MRI IMAGES. CALCULATE VOLUME OF LEAKED BLOOD. — 20

EXTRACT 3D DISTRIBUTION OF MAIN CEREBRAL ARTERIES FROM CTA/MRI IMAGE — 30

EXTRACT 3D DISTRIBUTION OF SUBARACHNOID SPACE FROM MRI IMAGE — 40

COLLECT SEGMENTATED CT/CTA/MRI IMAGE DATE TO TRAIN AUTOMATIC SEGMENTATION ALGORITHM. — 50

APPLY MACHINE LEARNING ALGORITHM FOR AUTOMATIC SEGMENTATION OF CT/CTA IMAGES — 60

CALCULATE GENERATION OF BLOOD BREAKDOWN PRODUCTS FROM LEAKED BLOOD — 70

CALCULATE WASH OUT (CONCENTRATION CHANGES) AND SPREADING OF BLOOD BREAKDOWN PRODUCTS WITHIN THE SUBARACHNOID SPACE — 80

IDENTIFY CRITICAL ZONES OF HIGH CONCENTRATION OF BLOOD BREAKDOWN PRODUCTS (EARLY LOCALISATION OF VASOSPASM AND DCI) — 90

IDENTIFY TIME OF CRITICAL ZONES FORMATION (EARLY FORCASTING OF VASOSPASM MOMENT) — 100

PROVIDE EARLY WARNING OF CEREBRAL VASOSPASM OCCURRENCE AND DCI (LOCATION AND TIME) — 110

METHOD AND APPARATUS FOR EARLY WARNING OF CEREBRAL VASOSPASM AFTER SUBARACHNOID HEMORRHAGE

FIELD OF INVENTION

The present invention is directed generally to a method and apparatus for early warning of cerebral vasospasm after subarachnoid hemorrhage.

BACKGROUND OF THE INVENTION

The invention includes a new process and apparatus to treat patients before they suffer a cerebral vasospasm.

Cerebral vasospasm (CV) and delayed cerebral ischemia (DCI) are typical phenomena occurring in the human brain within 3-21 days after an aneurysmal subarachnoid hemorrhage (SAH). Blood leaked after an aneurysmal rupture spreads out in SAS and perivascular space due to cerebrospinal fluid (CSF) flowing from cerebral ventricles.

In days 3-5 after the SAH, biologically active compound, oxy hemoglobin, is released during the process of breakdown of leaked blood provoking inflammatory reactions in perivascular space and triggering vasospasm in larger cerebral arteries and/or formation of delayed cerebral ischemia.

Pathological changes in intracranial arteries occurring during vasospasm contain narrowing of the artery lumen (vasoconstriction), thickening the artery wall, and impaired wall relaxation. In days 3-5 after SAH, oxy hemoglobin and bilirubin oxidation products—a red blood cell breakdown product-inhibit nitric oxide (physiologic vasodilator) and stimulates leukocytes to produce endothelin-1 (physiologic vasoconstrictor), resulting in potent vasoconstriction. Furthermore, the breakdown of oxyhemoglobin leads to a release of reactive oxygen species and iron which leads to oxidative damage to blood vessel walls. In addition, the production of vasoactive compounds after SAH, such as serotonin, norepinephrine, and angiotensin II, leads to potent vasoconstriction.

Additional processes following cerebral vasospasm are impaired vascular reactivity and a fall in cerebral blood flow. If the reduction in flow is severe enough, ischemia and infarction follow. The term "delayed cerebral ischemia" or "delayed ischemic neurologic deficit" describes the clinical situation where these multiple factors cause ischemia.

Current methods are not capable of providing reliable early warning of cerebral vasospasm and delayed cerebral ischemia. Existing methods allow only to provide information on the presence of active cerebral vasospasm. Detection for active vasospasm typically consists of serial neurologic exams, measurement of blood flow velocities by transcranial Doppler (TCD), Computed Tomography Angiography (CTA) or catheter angiography. Also, CTA or TCD techniques are used for the identification of vasospasmic artery and localization of vasospasmic segment of artery.

Current management of vasospasm involves prophylactic measures (applying vasopressors (nimodipine), thrombolytic agents (e.g., urokinase) and anti-inflammatory agents) or aggressive intervention. Intervention measures are applied when active vasospasm is detected and localized. Interventional techniques include mechanical or pharmacological vessel dilatation in the detected vasospasmic artery. Mechanical vasodilatation is achieved by means of transluminal balloon angioplasty and is directed towards a circumscribed proximal vessel segment allowing to forcibly dilate constricted vessels and restore perfusion to the affected (ischemic) brain regions.

Pharmacological endovascular dilatation is based on the continuous intraarterial infusion of vasodilatation agents (intra-arterial nicardipine, verapamil, nimodipine, and milrinone) via a microcatheter positioned within the proximal intracranial vessel territory affected by vasospasm.

Additional interventional treatment is the purification of cerebrospinal fluid by removing or neutralization of target compounds from CSF within cerebrospinal space. These target compounds are breakdown products of leaked blood (oxyhemoglobin, deoxyhemoglobin, vasoactive inflammatory products and toxins). Such treatment is based on long term (up to 10 days) injection of urokinase and ascorbic acid through the irrigation tubes placed in the Sylvian fissure (inlet) unilaterally or bilaterally and in the prepontine or chiasmal cistern (outlet) to clean blood breakdown products from CSF.

However, vasospasm remains an important determinant of outcome after cerebral aneurysm rupture. Early warning and early localization of cerebral vasospasm are necessary to personalize patient treatment after SAH to avoid vasospasm occurrence and delayed cerebral ischemia. Improving early warning of cerebral vasospasm in patients would improve treatment methods and patient outcomes.

BRIEF SUMMARY OF THE INVENTION

The invention includes a method and ITC-system for early warning of cerebral vasospasm and DCI including early localization of the most likely zones and arteries of cerebral vasospasms and DCI formation.

The inventive method includes the identification of subarachnoid space in a patient and the spread of blood leaked within subarachnoid space (SAS) by applying manual or automated segmentation technique of brain tomography images (Computed tomography (CT), Computed tomography angiography (CTA), Magnetic resonance imaging (MRI)); leading to early detection of brain zones with increased risk of cerebral vasospasm and delayed cerebral ischemia (DCI).

The inventive apparatus includes a system such as an Information and Communication Technology ICT-system, that can provide early warning of cerebral vasospasms and delayed cerebral ischemia based on automatic processing of MRI/CT/CTA images and patient specific data. Provided information on early warning of cerebral vasospasms and delayed cerebral ischemia includes identified specific segments of cerebral arteries with increased risk of cerebral vasospasms occurrence at specific time moments and specific zones of cerebral vasculature with increased risk of ischemia formation. Provided information is applied for patient-specific treatment and monitoring, such as endovascular administration of intra-arterial vasodilators and balloon angioplasty in identified specific cerebral arteries with increased risk of vasospasms, purification of cerebrospinal fluid, and brain oxygenation monitoring in specific zones of cerebral vasculature with increased risk of ischemia formation.

The invention is based on the determination of personalized geometry of subarachnoid space (SAS), the determination of leaked blood in SAS and brain parenchyma regions, the determination of wash out and migration of leaked blood in SAS due to CSF flow and the determination of changes of concentration of blood breakdown products in SAS.

BRIEF DESCRIPTION OF THE DRAWINGS

FIG. 1 is a flow chart describing the steps of the method for early warning of cerebral vasospasm occurrence.

DETAILED DESCRIPTION OF THE INVENTION

Figure 2:
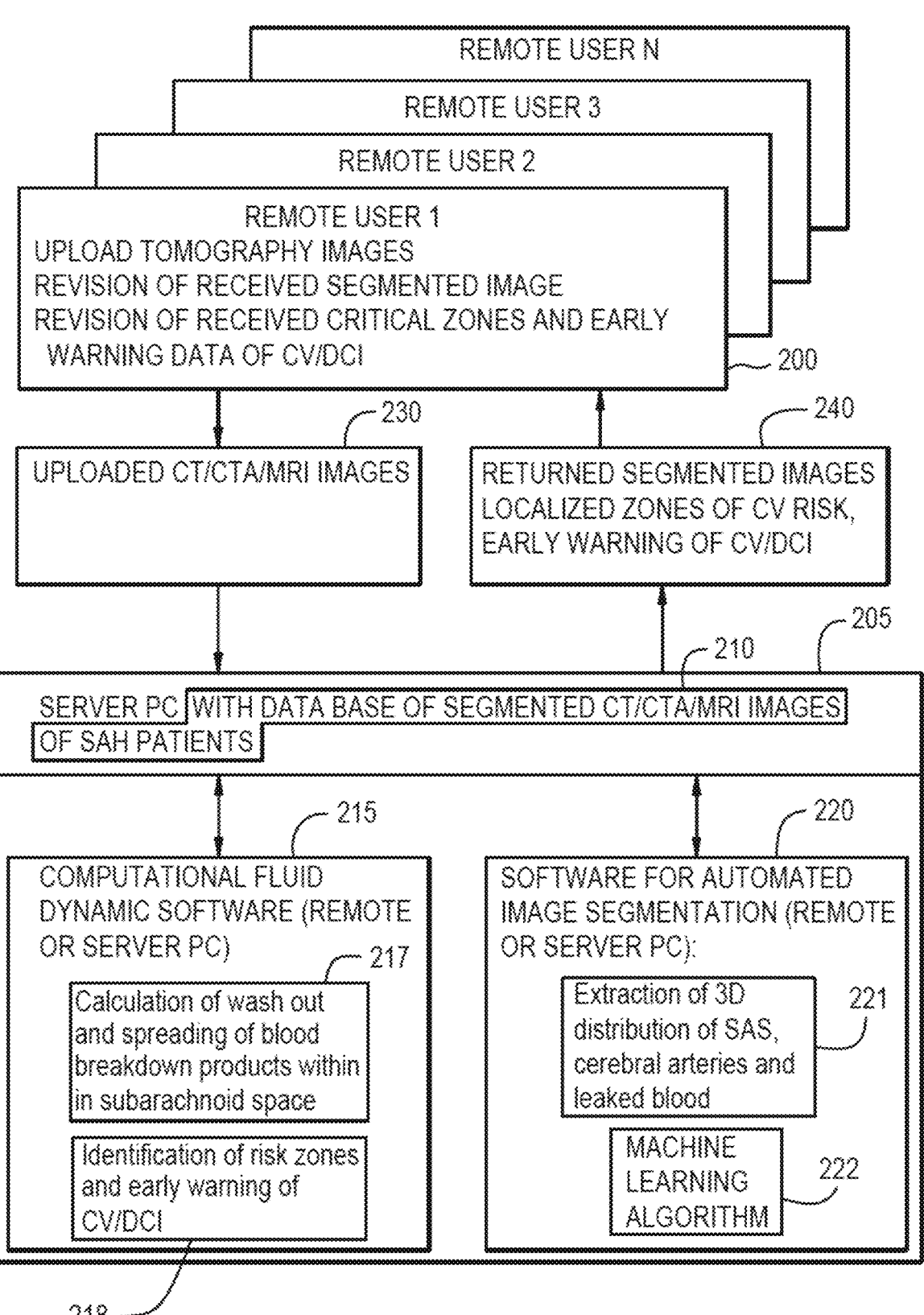
FIG. 2 is a structural diagram of the device for early warning of cerebral vasospasm.

The inventive apparatus is configured to identify specific segments of cerebral arteries that have an increased risk of the cerebral vasospasms occurrence at specific time moments and to identify specific zones of cerebral vasculature that have an increased risk of ischemia formation by using a novel and unique numerical model, which calculates the spreading and washing out of leaked blood breakdown products within subarachnoid space following after subarachnoid hemorrhage and identifies brain zones with increased risk of cerebral vasospasm and delayed ischemia formation according to the concentration of blood breakdown products.

Abbreviations used in the description of the invention include:

BBPs—Blood breakdown products
CSF—cerebrospinal fluid
CV—cerebral vasospasm
CT—Computed tomography
CTA—Computed tomography angiography
DCI—delayed cerebral ischemia
HU—Hounsfield units
MRI—Magnetic Resonance Imaging
SAH—subarachnoid hemorrhage
SAS—subarachnoid space
3D—three-dimensional The invention contemplates the analysis of preoperative CT/CTA images, such as those obtained before aneurysm clipping surgery, and MRI images of patients with aneurysmal SAH can provide information on the distribution of leaked blood within SAS, which can be used to identify distribution of blood breakdown products within SAS in time domain. Blood breakdown products such as those containing oxyhemoglobin, bilirubin oxidation products, and, endothelin-1 are involved in toxic redox reactions leading to vasospasm and vasculopathy. The concentration of blood breakdown products within SAS changes over time due to its wash out by flowing CSF.

The role of CSF which is produced continuously in brain ventricles is to wash away harmful waste proteins that build up between brain cells during waking hours. After SAH, the flowing CSF spreads blood breakdown products of leaked blood and changes their concentration within SAS over time. Remains of blood breakdown products left in specific points of SAS close to cerebral arteries release biologically active compounds, such as oxyhemoglobin and bilirubin oxidation products, which can cause vasospasm in proximate arteries which later develop to ischemia. The concentration of blood breakdown products changes over time in SAS.

The risk of cerebral vasospasm at a specific location in SAS close to the cerebral artery is related to the concentration of the BBPs at that location. The higher the BBPs concentration means the higher the risk of vasospasm formation. The concentration of the BBPs is directly related to the distribution of leaked blood density over subarachnoid space and its spreading by CSF. The volume of hemorrhage is determined from CT image performing its segmentation.

The threshold defining the "high" concentration is estimated empirically from data from a pilot study. The pilot study included data from 28 SAH patients. High BBPs concentration is determined by calculating BBPS concentrations on detected actual vasospasm and ischemia places from CT images.

The inflammation process may also start in surrounding microvasculature regions close to regions of increased concentration of spreading blood breakdown products, thus leading to the formation of ischemic zones. Early identification of regions of increased concentration of blood breakdown products within SAS can be used for the early personalized treatment of SAH patients.

FIG. 1 shows the method of how the early warning of CV and DCI is performed. First, there is an acquisition and gathering of preoperative CT/CTA and MRI images 10 of leaked blood within the subarachnoid space. This is followed by the extraction of 3D distribution of leaked blood from within the subarachnoid space from CT and MRI images 20. These images are used to calculate the volume of leaked blood. Patient specific 3D distribution of leaked blood is reconstructed from an automatically segmented preoperative CT image of SAH patient 20. The volume of leaked blood is determined from an automatically segmented CT image by integrating the segmented spatial distribution of leaked blood within subarachnoid space.

Extracted from the CTA/MRI images is the 3D distribution of main cerebral arteries 30. Patient-specific 3D distribution of cerebral arteries is reconstructed from an automatically or manually segmented preoperative CTA image 30. The 3D of the subarachnoid space is extracted from the MRI images 40. Patient-specific 3D distribution of the subarachnoid space is reconstructed from an automatically or manually segmented MRI image 40.

Segmentation is performed by partitioning volumes of leaked blood, cerebral arteries and subarachnoid space in three-dimensional tomography images. Spatial distribution of different anatomical structures is determined according to their different radio intensive characteristics expressed in Hounsfield Units (HU) considering the specificity (density) of segmented anatomic structure.

In a CT scan, Hounsfield Unit is proportional to the degree of x-ray attenuation and it is allocated to each pixel of tomography image which represents the density of the tissues. Each pixel HU value undergoes a linear mapping to grayscale level between 0 and 255 (ranging from white to black).

In the CT image, the matrix of reconstructed linear attenuation coefficients ($\mu$_material) is transformed into a corresponding matrix of Hounsfield Units (HU material), where the HU scale is expressed relative to the linear attenuation coefficient of water at room temperature ($\mu$_water). For example, the specific CT HU intensity of the cerebrospinal fluid (CSF), defining the subarachnoid space, ranges from 0 to +15. The cerebral arteries are filled with blood, therefore, their specific CT HU intensity ranges are from +30 to +55 HU. Subarachnoid hemorrhage's (extravascular leaked blood) specific CT HU intensity ranges from +65 to +95].

Multiple CT images of an individual patient are used for 3D reconstruction of subarachnoid hemorrhage distribution. The CT image consists of multiple slices of cross-sectional images each slice shows the cross-section at a different depth. CTA or MRI images are used for 3D reconstruction of cerebral arteries of individual patients. CTA is typically used for reconstruction of cerebral arteries. CTA is used with a contrast agent, that is injected into the blood stream for clearer visualization of arteries.

The 3D reconstruction of subarachnoid space can be obtained from segmented high-resolution MRI images of an individual patient. The MRI scan can be a preoperative MRI scan or a MRI scan made within 3 days after an aneurysm rupture. The MRI is taken before the risk of vasospasm occurrence. The subarachnoid space could also be obtained by using available spatial models of SAS geometry. The inventors used a spatial model of subarachnoid space obtained from their own patient data. It is also possible to use general models of subrachnoid space available from free online databases, such as MPI-CBS: https://openscience.cbs.mpg.de/bazin/, PLOS-One quantity and quality: normative open-access neuroimaging databases https://journals.plos.org/plosone/article?id=10.1371/journal-.pone.0248341, or commercial available databases that include segmentation service: https://www.medseg.ai/).

Segmentation of CT/CTA/MRI images is performed using an automated method based on HU analysis and prior knowledge of cerebral anatomy. Segmentation of CT scans are performed by a trained neural network 60. Training of the neural network is performed using a dataset of CT scans 50 from multiple patients, which were segmented by experienced radiologists. Datasets were obtained from two different hospitals.

The neural network architecture is UNet with a backbone called ResNet101. The segmentation algorithm works as follows: a CT scan (sagittal plane images are 512 pixels by 512 pixels of the patient is loaded to the algorithm, which uses the neural network to predict the likelihood of a pixel indicating a hemorrhage. The output of the neural network is an array, of the same dimension as the input CT scan, where each pixel has a value between 0 and 1 assigned to it. 0 indicates that the corresponding pixel does not belong to the hemorrhage, any positive value (up to 1) indicates how likely that the corresponding pixel belongs to the hemorrhage. Another step in the algorithm uses a threshold function with a threshold value equal to 0.5. This function acts as follows: each pixel, obtained from the neural network is scanned and if the likelihood that this particular pixel belongs to the hemorrhage is above 0.5, then the value is changed to 1, while the value is changed to 0, if the likelihood is below or equal to 0.5. The algorithm outputs then the original CT scan of the patient and a pixel array, of the same dimensions, each pixel of the pixel array has only values 0 or 1, where the value 1 of a pixel indicates that the corresponding pixel of the CT scan is predicted to belong to the hemorrhage locations. The output of the algorithm, the type of array, is called a segmentation mask.

The automated segmentation applies a machine learning algorithm for automatic segmentation of CT and CTA images 60. The automatic segmentation is performed with a neural network which is continuously trained on the new data in a supervised or semi-supervised manner. The network outputs a heatmap of the probability that a pixel (or voxel) belongs to the hemorrhage site. Once this heatmap is predicted the thresholding function is applied and a segmentation mask is returned as a prediction result.

In order to have a continuously learning system, which improves its predictions based on the new data and which adapts to the specific properties of the hospital CT equipment as well as to the specific population of patients, a semi-supervised learning is used.

In the semi-supervised learning part, the system saves a series of CT scans from previous patients that were treated for the same conditions. A pseudo-label approach is implemented when a system predicts a mask (a mask is the output of 0 and 1 values of the algorithm as described above). This new information is joined to the training dataset and the neural network is then retrained on this new dataset. A pseudo-label approach works as follows: hemorrhage masks are predicted for a series of patients; these masks are treated as correct/true locations of hemorrhage.

After segmentation there is a calculation of wash out and spreading of blood breakdown products (BBPs) within subarachnoid space. First, the generation of blood breakdown products is calculated from the spatial distribution of the leaked blood 70. Time-dependent spatial distribution of BBPs concentration is determined in specific areas of subarachnoid space at specific time moments by calculating wash out and spreading of BBPs within the subarachnoid space 70. The time-dependent spatial distribution of blood breakdown products (BBPs) in SAS is determined by calculating the generation of BBPs in a leaked blood clot, their diffusion and advection by CSF flow within SAS.

CSF flow and BBPs transport through SAS are determined by standard methods of Computational Fluid Dynamic (CFD) (e.g., Darcy's law, etc.), which allows estimating CSF hydrodynamic pressure and velocity distribution. The calculation is performed by solving a system of partial differential equations (PDEs) consisting of conservation of mass and momentum together with species transport equations.

The equations expressing CSF flow and BBPs transport through SAS and leaked blood clot in terms of Darcy's law and BBPs species transport equation are as follows:
Conservation of mass:

$$\frac{\partial(\epsilon_p \rho)}{\partial t} + \nabla \cdot (\rho u) = Q_m \tag{1a}$$

$$\partial(\epsilon_p \rho)/\partial t + \nabla \cdot (\rho u) = Q_m \tag{1b}$$

Conservation of momentum:

$$u = -\frac{\kappa}{\mu} \nabla p \tag{2}$$

7

Transport of species:

$$\frac{\partial(\epsilon_p c_i)}{\partial t} + \frac{\partial(\rho c_{P,i})}{\partial t} + u \cdot \nabla c_i = \nabla \cdot [D_{e,i} \nabla c_i] + R_i + S_i, \quad (3a)$$

$$i = 1, 2, 3, \ldots, N_p$$

$$\partial(\varepsilon_p c_i)/\partial t + \partial(\rho c_{P,i})/\partial t + u \cdot \nabla c_i = \nabla \cdot [D_{e,i} \, \nabla c_i] + R_i + S_i, \quad (3b)$$

$$i = 1, 2, 3, \ldots, N_p$$

where ■ is the placeholder, $$\frac{\partial}{\partial \blacksquare}$$

is the partial differential, $\varepsilon_p$ is the combined porosity of SAS and leaked blood clot, $\rho$ is the density of CSF, $\nabla \cdot \blacksquare$ is the divergence, u is the velocity vector of CSF flow, $Q_m$ is the CSF mass source, $\kappa$ is the permeability of SAS and leaked blood clot, $\mu$ is the viscosity of CSF, $\nabla \blacksquare$ is the gradient, p is the pressure of CSF, $c_i$ is the molar concentration of i-th BBPs species, $c_{p,i}$ is the amount of molar concentration adsorbed to solid medium of i-th BBPs species, $D_{e,i}$ is the effective diffusion of i-th BBPs species (including molecular diffusion $D_{D,i}$ of i-th BBPs species and augmented by dispersion due to porosity and CSF velocity pulsations), $R_i$ is the reaction rate of i-th BBP species, Si is the source term of i-th BBP species, Np is the number of BBP species.

Patient-specific data of a hemorrhagic patient, consisting of hemorrhage distribution segmented from medical imaging data (Hounsfield Units), and blood test results (hematocrit level, fibrin) are used to specify leaked blood clot (density, permeability, porosity) and BBPs generation rate. The aforementioned data is used to determine initial and boundary conditions for the calculation of BBPs concentration and modeling of BBPs spreading.

Specifically, the HU values are used to categorize the density of hemorrhagic blood. Higher HU values correspond to higher blood density. Extravascular (leaked) blood, however, clots rapidly, and as plasma is extruded and resorbed from the clot, the concentration of the hemoglobin protein can double and triple, so that intracranial hemorrhage typically measures 60-90 HU. The porosity and permeability of the blood clot are calculated based on the HU values and data of blood test results (e.g. the hematocrit level, fibrin concentration, etc.). Both, the porosity and permeability of the blood clot are dependent on the HU and hematocrit values and, in general, are higher when the HU values are lower and also are higher when the hematocrit values are lower.

The BBPs generation rate (concentration) in each point of the blood clot depends on hematocrit concentration at this point and is calculated according to the HU values and the hematocrit level. The BBP generation rate is dependent on the HU and hematocrit values and, in general, is higher when the HU value is higher and also is higher when the hematocrit values are higher.

The inventive method then conducts a calculation of BBPs concentration and spread, which is associated with the increased risk of cerebral vasospasm and delayed cerebral ischemia 80. The method calculates wash out, spreading and concentration changes over time of BBP within the subarachnoid space 80.

The risk of cerebral artery vasospasm and delayed cerebral ischemia is related to the concentrations of BBPs, which are changing in time and space within the subarachnoid space. Higher concentrations of BBPs close to the specific cerebral artery can trigger vasospasm in the artery. The next step of the inventive method identifies critical zones of high concentrations of BBP which identifies early localization for potential locations for vasospasm and DCI 90.

The time-dependent spatial distribution of BBPs concentrations is determined from the calculation of CSF flow and BBPs transport. Location, time and duration of critical zones, associated with higher risk of CV and DCI, are determined by locating zones of high BBPs concentrations.

Distribution of BBPs concentration provides the 3D map of CV and DCI probability as follows:

$$P_{risk}(r_a, t) = F(c_i(r - r_a, t), D_a(r_a), C_a(r_a))$$

where r is the position vector, $r_a$ is the position closest artery wall, $P_{risk}(r_a, t)$ is the map of DCI and CV probability, F is the function determining integrative relationship between DCI and CV probability and the set of influential factors: BBPs species concentration around cerebral arteries $c_i(r-r_a, t)$, the diameter of the cerebral arteries $D_a(r_a)$, calcination level of the cerebral arteries $C_a(r_a)$.

The time of the critical zones formation is also identified by the method and apparatus permitting early forecasting of a vasospasm moment 100. The probability of cerebral vasospasm is determined in specific areas that are close to cerebral arteries at specific time moments according to determined zones with high concentration level of BBPs.

The method provides an early warning of CV occurrence and DCI location and time 110. The device apparatus provides a warning when the calculated risk factor is above 0.5 at any specific brain zone. The operator can visualize the 3D map of risk zone to examine the images and view them at the desired angles to identify the high risk zones. The probability of delayed cerebral ischemia is determined in specific areas of cerebral vasculature at specific time moments according to determined zones with high concentration level of BBPs. The probability of delayed cerebral ischemia is determined in specific areas of cerebral vasculature where blood flow is maintained from identified vasospasmic artery 110.

The obtained information on the distribution of BBPs concentration and 3D map of CV and DCI probability within subarachnoid space adjacent or close to specific places of cerebral arteries and adjacent or close to specific zones of vascular territories can be used to provide an early warning of cerebral vasospasm as well as for personalized patient management in order to prevent the occurrence of cerebral vasospasms and formation of ischemic zones. Similarly, the obtained information on the probability of cerebral vasospasms and delayed cerebral ischemia is also used for patient-specific and precise treatment to prevent occurrence of cerebral vasospasms and delayed cerebral ischemia.

Personalized management of SAH patient can include several types of treatment techniques. The treatment techniques include, but are not limited to, interventional techniques, CSF purification techniques and brain monitoring techniques. For example, interventional techniques can include mechanical or pharmacological vessel dilatation in the specific cerebral arteries with early identified risk of vasospasm occurrence. Examples include endovascular administration of intra-arterial vasodilators in identified specific cerebral arteries with increased risk of vasospasms or endovascular balloon angioplasty in identified specific cerebral arteries with increased risk of vasospasms.

Additionally, CSF purification techniques can be used with the invention used to localize optimal places for insertion of irrigation tubes into specific zones of subarachnoid space with high BBPs concentration. For example, purification of cerebrospinal fluid in specific zones of cerebral vasculature with increased risk of delayed cerebral ischemia formation can be conducted.

Further, techniques such as brain oxygenation monitoring techniques can be used by inserting oxygenation monitoring sensors into specific brain vascular territories where there is a high risk of ischemic zone formation.

An example of the method being applied to a patient in a patient care setting is shown in FIG. 1. The first step is acquiring set of images from neuroimaging scans of SAH patient after aneurysmal rapture (CT, CTA or MRI images) performed after patient admission to radiology department 10. Images are then analyzed to extract 3D distribution of leaked blood with subarachnoid space. A 3D distribution of leaked blood within subarachnoid space is reconstructed from CT images (or MRI if available) by performing automated segmentation 20. Images are then analyzed to extract 3D distribution of cerebral arteries. The 3D distribution of cerebral arteries is reconstructed from CTA images (or MRI if available) by performing automated segmentation 30. Images are analyzed to extract 3D distribution of subarachnoid space 40. 3D distribution of subarachnoid space is reconstructed from MRI images (obtained within 3 days after aneurysm rapture) or taken from available databases of spatial models of SAS geometry. Segmented images are then collected and used to form database which is used to train a machine learning algorithm for automatic segmentation 50, 60. Extracted spatial distribution of leaked blood is used to calculate generation of blood breakdown products (BBPs) from a leaked blood clot 70. The wash out and spreading of BBPs within reconstructed subarachnoid space due to CSF flow within SAS is calculated by solving Darcy's equations allowing to estimate the time-dependent spatial distribution of BBPs within SAS 80. The zones with high concentrations of BBPs close to specific cerebral arteries are determined for specific time moments as higher risk zones associated with cerebral vasospasm and early formation of delayed cerebral ischemia 90, 100. The diagnostic information of time and location of higher risk zones formation associated with cerebral vasospasm and delayed cerebral ischemia is provided to clinical physicist and radiology department 110.

FIG. 2 is a structural diagram of the apparatus for early warning of cerebral vasospasm and DCI. The apparatus consists of a series (1 . . . . N) remote users 200 that have connected with a computer system with a processor such as a server or a PC with a processor 205. The computer system 205, includes a data base of reference tomography images 210, of segmented CT/CTA/MRI images of SAH patients, software configured for computational fluid dynamics calculations 215, and software configured for automatic tomography image segmentation 220. The software for computational fluid dynamic calculation 215 and software with automatic tomography image segmentation 220 can be installed on a computer system PC 205 or launched on separate remote PCs. The remote users 200 can upload brain tomography images of SAH patients (CT/CTA/MRI) 230 to the server PC 205. The remote users 200 then receive image analysis information that results from automatic image segmentation and diagnostic information related to localization of critical vasospasmic and ischemic risk zones and early warning of CV/DCI 240. Uploaded images 230 are processed with software for automatic images segmentation 220 that allows to extract 3D information on leaked blood, cerebral arteries and subarachnoid space 221. The software for automatic images segmentation 220 is configured to also include a machine learning algorithm for automatic segmentation of CT and CTA images 222.

The reference database of the segmented brain scan images 210 is used to train the automatic segmentation algorithm which is used for 3D reconstruction of leaked blood, cerebral arteries and subarachnoid space from brain tomography images (CT/CTA/MRI) 260. The remote user 200 can review the results of segmentation 240. Newly segmented images are revised and can be included into the reference database of segmented images 210 to increase the reliability of the automatic segmentation algorithm 220.

The extracted 3D information on leaked blood, cerebral arteries and subarachnoid space is processed with software for computational fluid dynamics calculation 215. The software is configured to identify time-dependent wash out and spreading of leaked blood break down products within subarachnoid space 217. The apparatus conducts a calculation of washout and generates an early warning of when cerebral vasospasm and delayed cerebral ischemia is formed according to determined risk zones with high concentrations of BBPs close to specific cerebral arteries at specific time moments and patient-specific factors 218. The apparatus able to identify risk zones and transmit of a message or signal of an early warning of CV/DSI.

Figure 3A:
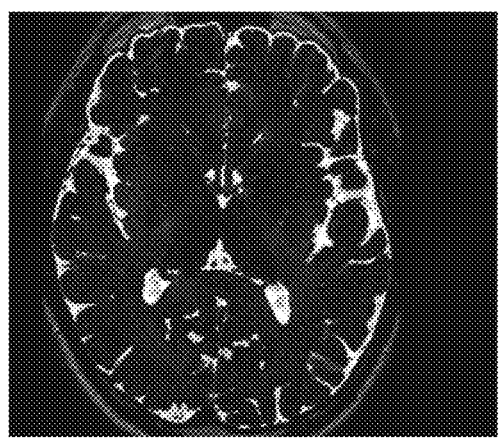
FIGS. 3A, 3B, 3C and 3D are extracted 3D distributions of subarachnoid space from MRI images.
Figure 3C:
Figure 3B:
Figure 3D:
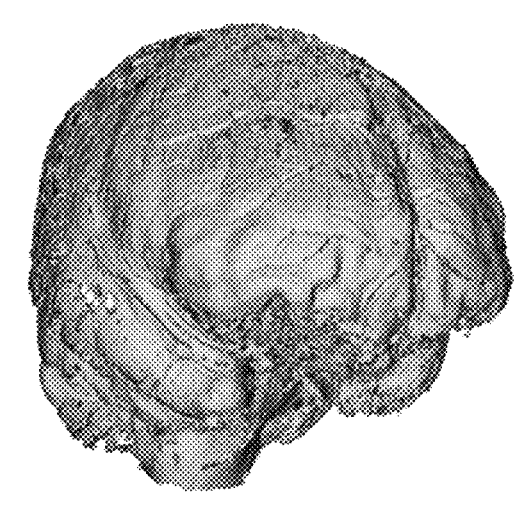

FIGS. 3A-3D show the extracted 3D distribution of subarachnoid space, which was obtained by performing segmentation of MRI image of SAH patient. 3D distribution of subarachnoid space is shown in axial plane FIG. 3A, in coronal plane FIG. 3B, in sagittal plane FIG. 3C and in a spatial three-dimensional view FIG. 3D.

Figure 4A:
FIGS. 4A, 4B, 4C and 4D are extracted 3D distributions of leaked blood from CT images.
Figure 4C:
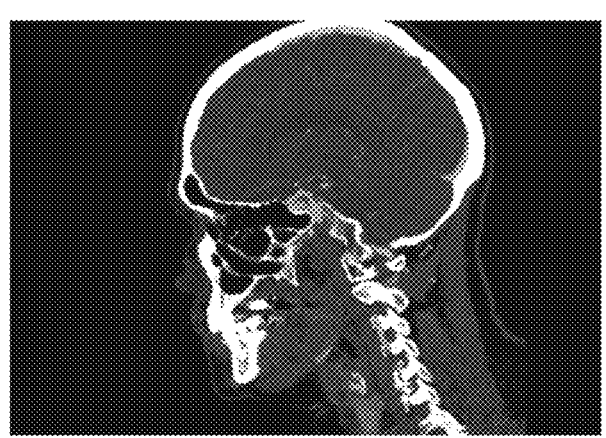
Figure 4B:
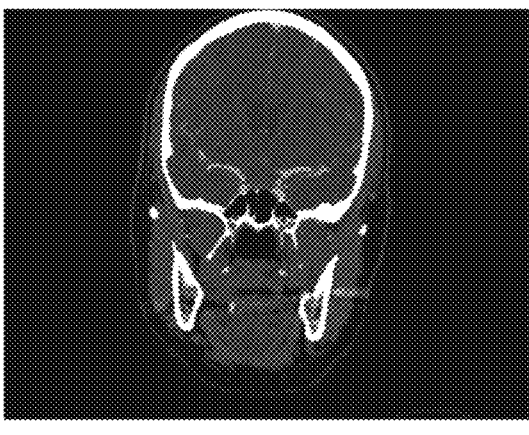
Figure 4D:
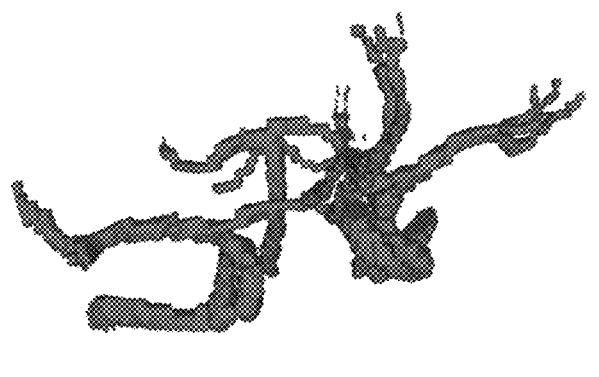

FIGS. 4A-4D show the extracted 3D distribution of cerebral arteries, which was obtained by performing segmentation of CTA image of SAH patient. 3D distribution of cerebral arteries is shown in axial plane FIG. 4A, in coronal plane FIG. 4B, in sagittal plane FIG. 4C and in spatial 3D view FIG. 4D.

Figures 5A, 5B, 5C, 5D:
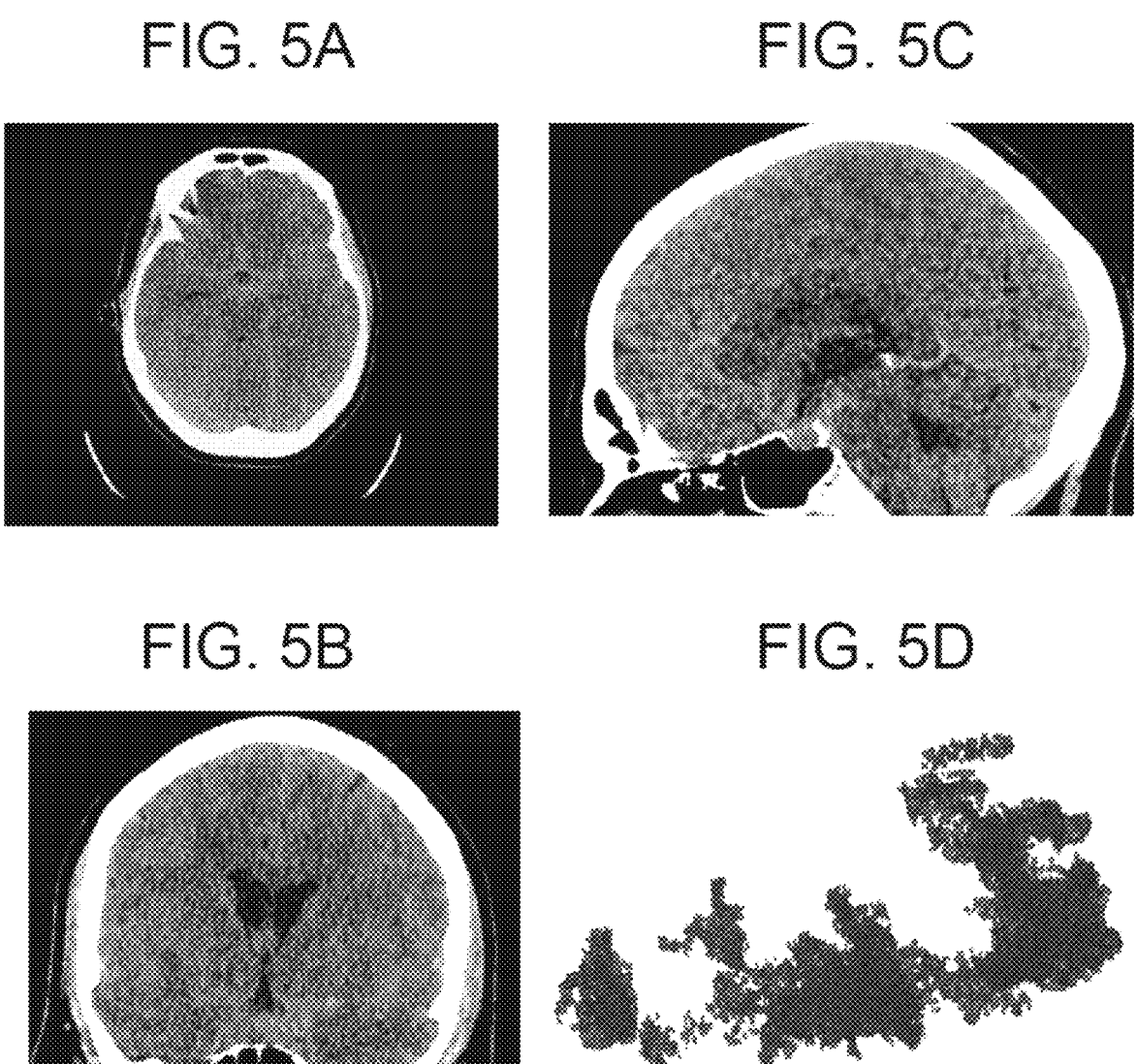
FIGS. 5A, 5B, 5C and 5D are extracted 3D distributions of cerebral arteries from CTA images.

FIGS. 5A-5D show the extracted 3D distribution of leaked blood (hemorrhage) within the subarachnoid space, which was obtained by performing segmentation of CT image of SAH patient. 3D distribution of leaked blood is shown in axial plane FIG. 5A, in coronal plane FIG. 5B, in sagittal plane FIG. 5C and in spatial 3D view FIG. 5D.

Figure 6:
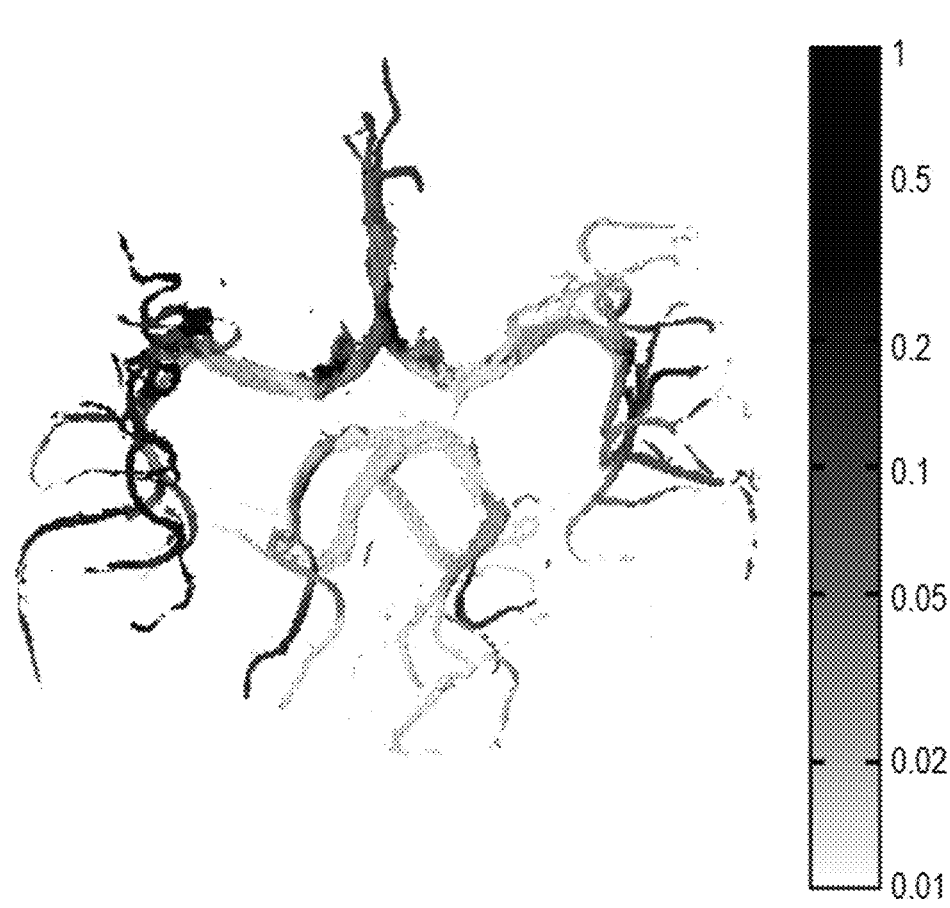
FIG. 6 is a calculated 3D distribution of blood breakdown products on cerebral artery walls within subarachnoid space.

FIG. 6 is an image of the calculated 3D distribution of blood breakdown products concentration on cerebral arteries at third day after a SAH. The concentrations of BBPs products are normalized according to the BBPs species concentration maximum (at third day). The 3D distribution and scale of normalized BBPs concentration are represented by grayscale with a grayscale legend on the right of the FIG. 6. Black color in the grey scale legends corresponds to maximum BBPs concentration (at third day). White color corresponds to zero BBPs concentration. This scale is also used for FIGS. 7 through 11.

To show the validity of the method, places of cerebral vasospasms and ischemic zones were identified by a professional radiologist after the examination of two CT/CTA scans, the first of which was made upon the arrival of the patient (1$^{st}$ day after SAH) and the second was made on the ninth day after a SAH. Vasospasms were identified by detected significant contraction. Vasospasm is categorized according to percentage of luminal contraction as mild (<30% luminal reduction), moderate (30% to 50% reduction), or severe (>50% reduction). In the invention significant refers to severe category when contraction is >50%. of cerebral arteries after comparing the diameter of the arteries in the first and the second scans. The places of significant contraction of cerebral arteries are marked as vasospasms in FIG. 7A as 701, 702, 703 and 704. The ischemic zones were identified and segmented based on the HU values and the anatomical knowledge of the radiologist.

Figure 7A:
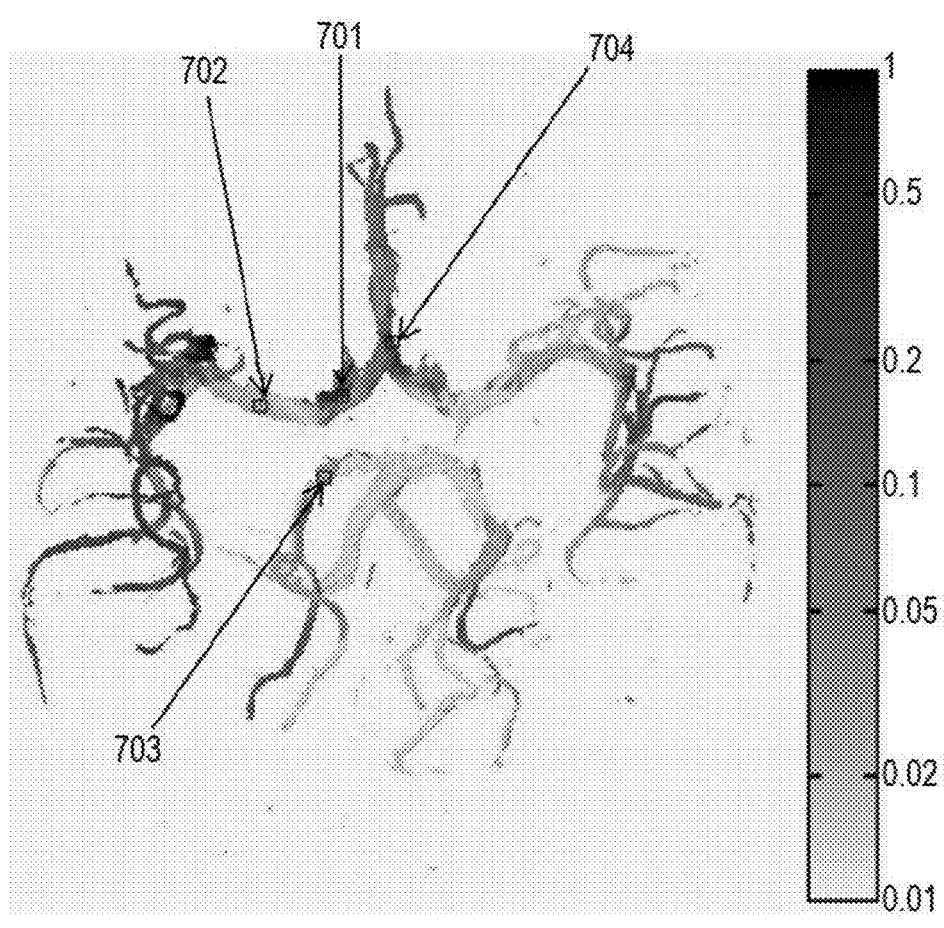
FIGS. 7A, 7B, and 7C are calculated 3D distributions of blood breakdown products on cerebral artery walls within subarachnoid space.
Figure 7B:
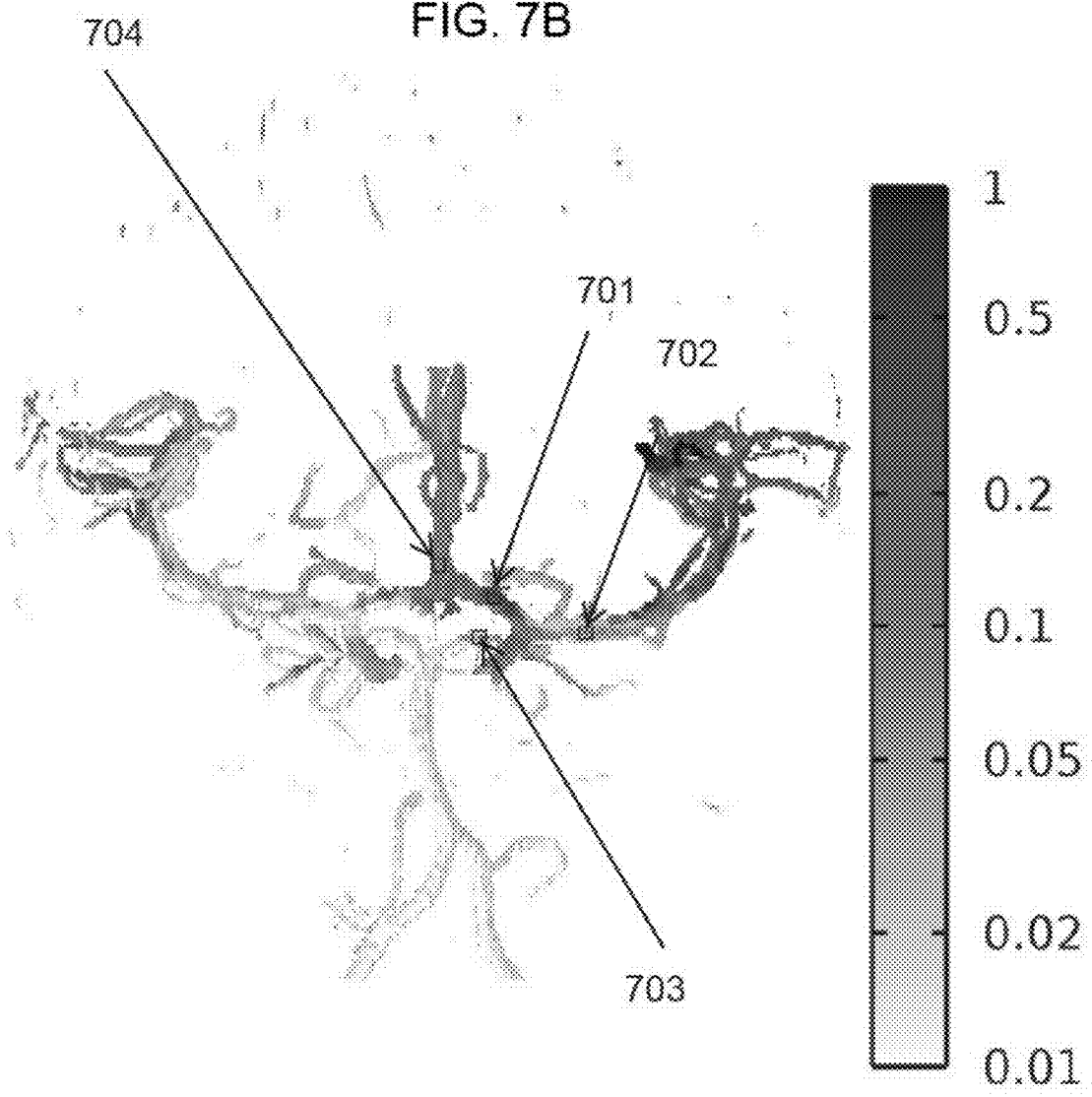
Figure 7C:
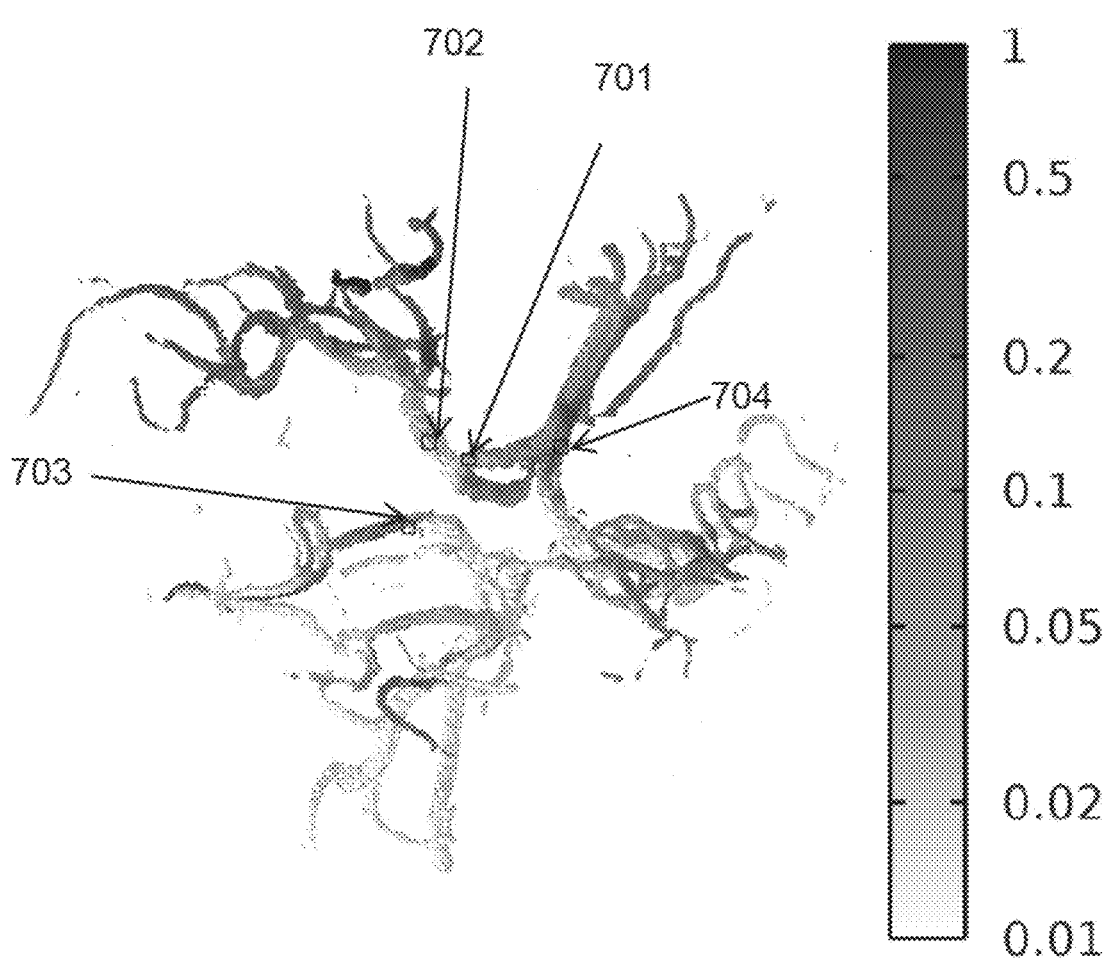

FIGS. 7A, 7B, and 7C are images of, from different angles of the calculated 3D distributions of blood breakdown products on cerebral artery walls at the third day after SAH. The marked points, 701, 702, 703 and 704 indicate locations where later formation of cerebral vasospasms occurred. The figures demonstrate the validity of the method by presenting the calculated BBPs concentration (third day after SAH) as in FIG. 6 and actual cerebral vasospasm locations marked as 701, 702, 703 and 704 were determined while an operator performed a CT/CTA scan at the ninth day after a SAH.

The predicted locations of cerebral vasospasm are based on the darker areas shown in the images. The detected locations of actual vasospasm locations marked as 701, 702, 703 and 704 are obtained from CTA image at 9th day according to the constriction of diameter in the larger anterior artery 701, 702 and 704 and posterior artery 703. Constriction of the arteies was confirmed by radiologist after analysis of the CTA image.

Figure 8:
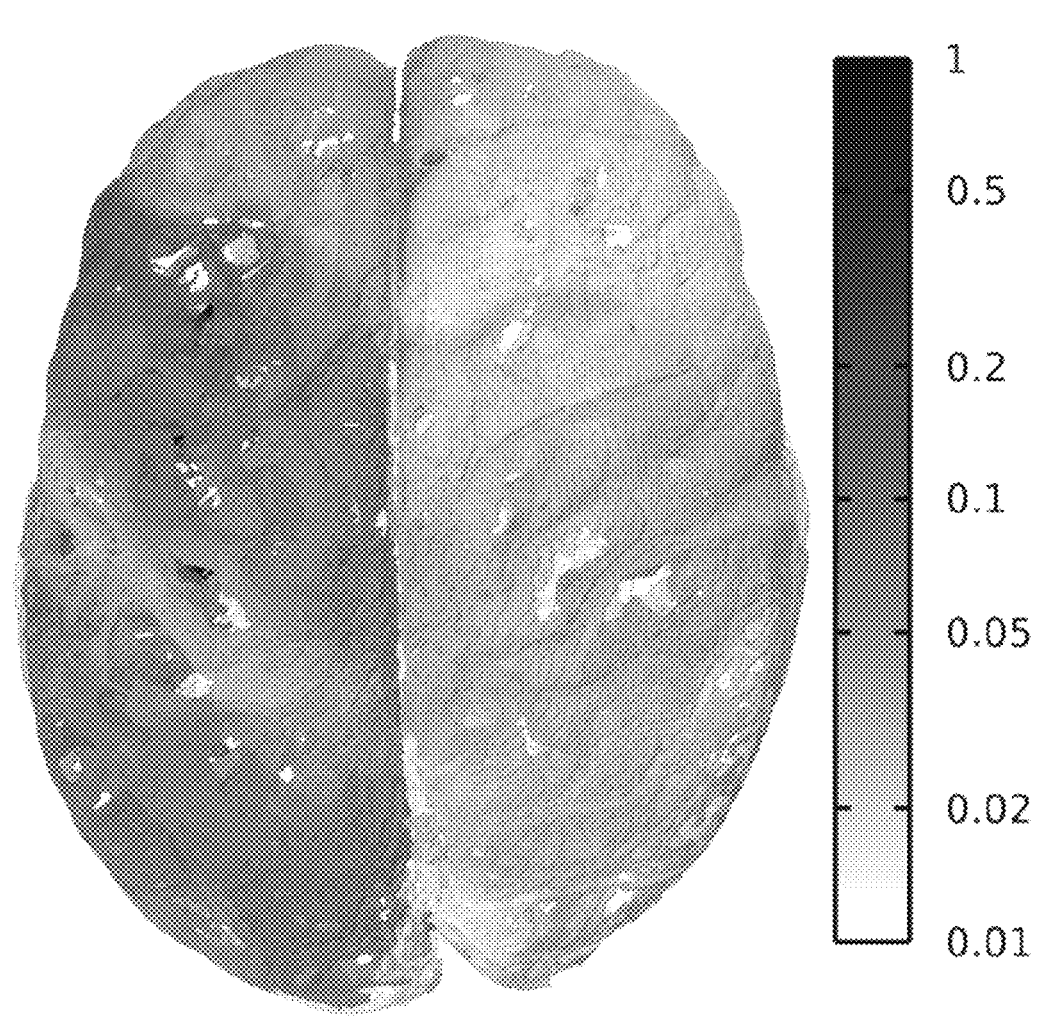
FIG. 8 is a calculated 3D distribution of blood breakdown products within subarachnoid space at 3rd day after SAH.

FIG. 8 is an image showing the calculated BBPs concentration within subarachnoid space (third day after a SAH). In FIG. 8 the left side of the brain was observed darker after calculating BBPs. The darker area in the figure shows the part of the brain that has higher risk of later developing of delayed cerebral ischemia.

Figure 9:
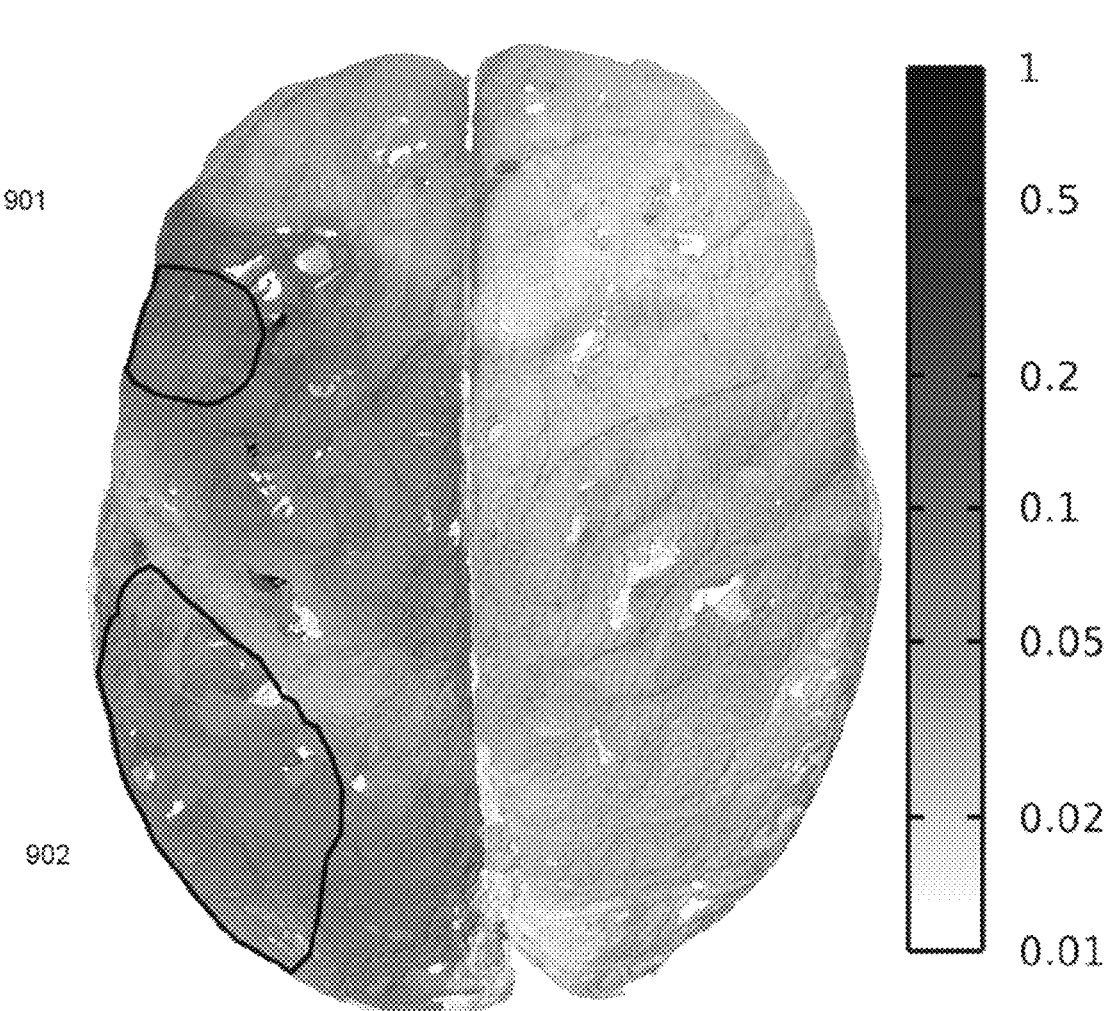
FIG. 9 is a calculated 3D distribution of blood breakdown products (BBPs) within subarachnoid space at 3rd day after SAH with marked zones of later formation of delayed cerebral ischemia.

FIG. 9, which is a modified version of FIG. 8, demonstrates the validity of the method by presenting BBPs concentration within subarachnoid space at the third day after a SAH. Ischemia was found while performing a CT scan on 9th day (FIG. 9). The black outlines indicate zones 901 and 902, where actual ischemic zones were detected from the CT image and marked by radiologists.

The actual ischemic zones were determined while performing a CT/CTA scan at ninth day after a SAH.

The detected ischemic zones 901 and 902 are results of ischemic zone segmentation from a CT scan made on the 9th day by a radiologist. The figure demonstrates that actual ischemic zones 901 and 902 occurred in the part of the brain where the high concentration of BBPs were calculated for both 3rd and 9th day.

The invention permits clinicians the ability to visualize the results of the calculated BBPs concentration around arteries and within subarachnoid space. The darker places are associated with risk of later formation of ischemic zones and vasospasms and indicate areas and locations appropriate for treatment. The figures show that the darker places on cerebral artery are factors for prognosing occurrence of actual cerebral vasospasms that occurred in the same artery at or close to darker places on the artery. In order to prevent cerebral vasospasms a clinician using the invention to locate high risk areas might choose intraarterial delivery of vasodilators in arteries to areas darker area or zones with higher BBPs concentration. The cerebral vasculature in critical brain zones with that have high BBPs concentration can be fed from other arteries with higher BPPs concentrations. The intraarterial treatment by vasodilator in a high risk predicted vasospasmic artery might also minimize risk of ischemia formation of vasculature and smaller arteries which are fed from that high risk vasospasmic artery.

Figure 10:
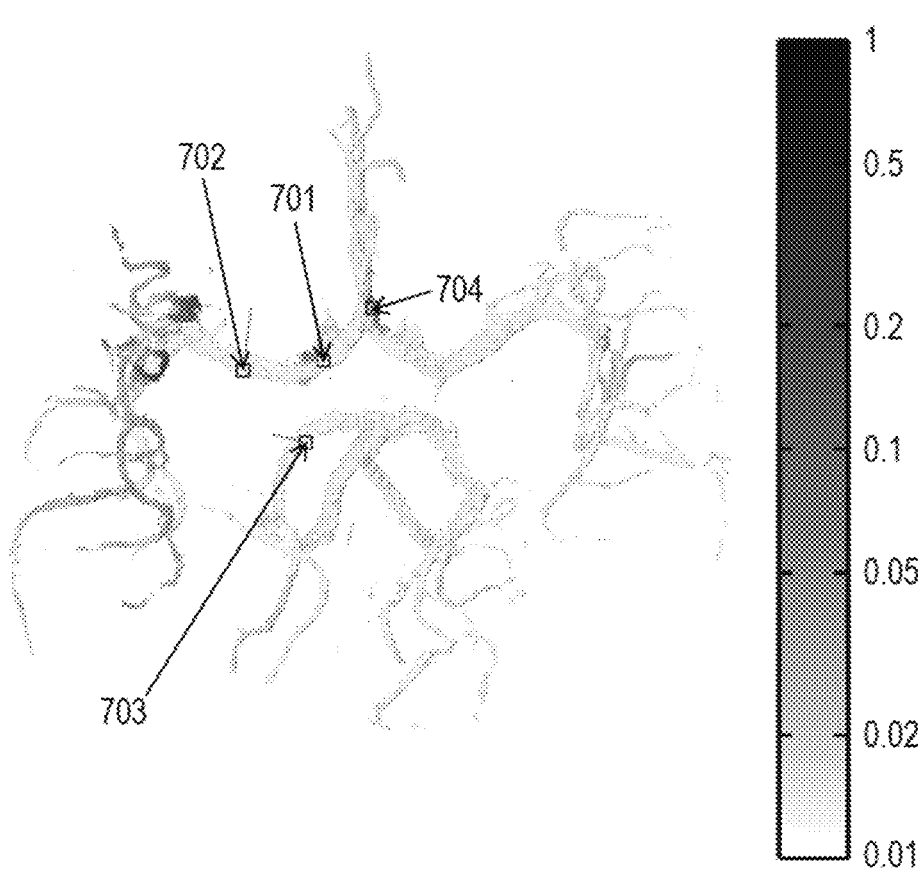
FIG. 10 is a calculated 3D distribution of blood breakdown products on cerebral artery walls at 9th day after SAH.

FIG. 10 shows the calculated BBPs concentration close to cerebral arteries (ninth day after a SAH). Actual cerebral vasospasm locations marked as (701, 702, 703, 704) determined while performing CT/CTA scan at ninth day after a SAH.

Figure 11:
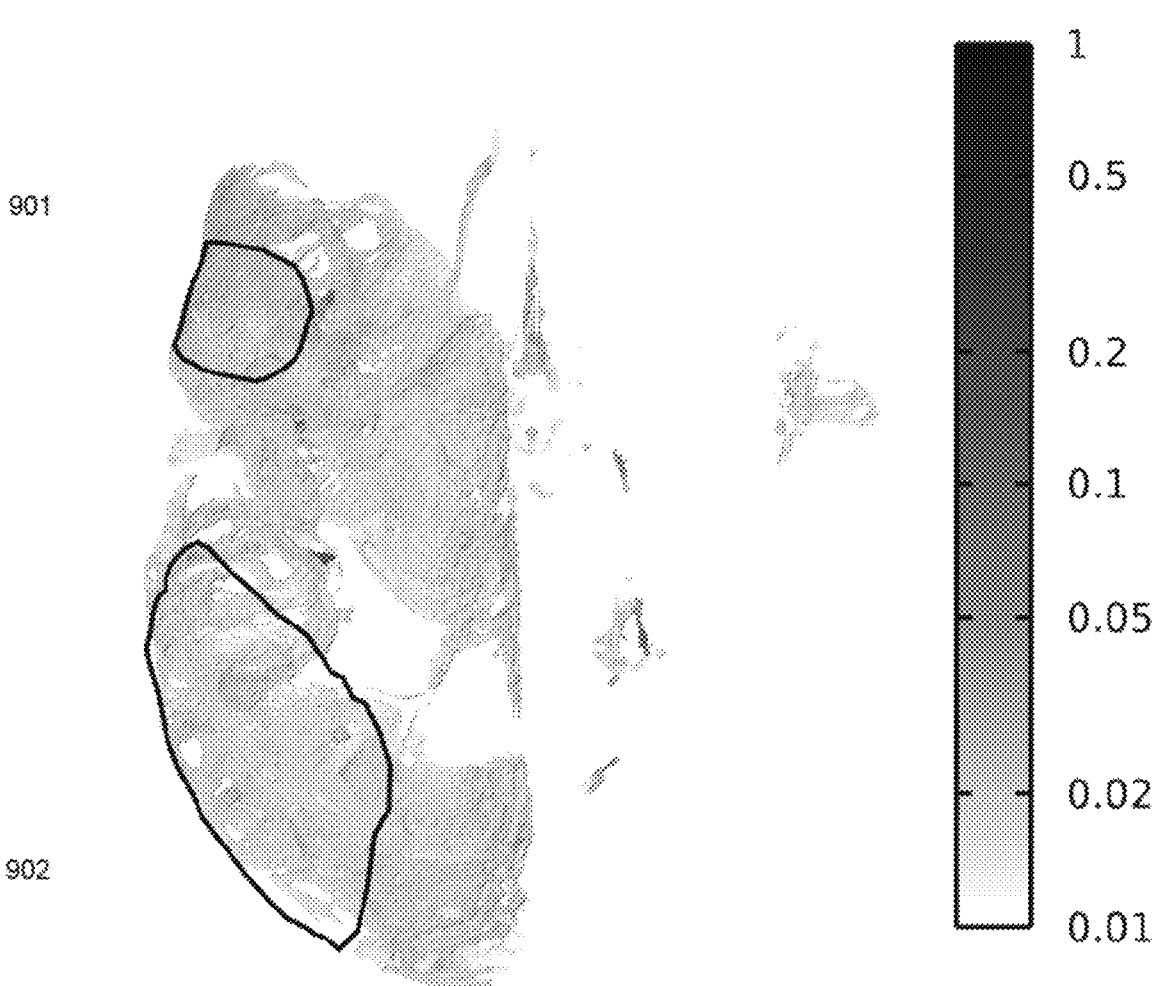
FIG. 11 is a calculated 3D distribution of blood breakdown products (BBPs) within subarachnoid space at 9th day after SAH.

FIG. 11 shows the calculated BBPs concentration within subarachnoid space on the ninth day after a SAH. Actual ischemic zone locations 901 and 902 are marked with black lines. Actual ischemic zones were determined while performing CT/CTA scan at ninth day after a SAH.

In FIGS. 6-11, the concentrations of BBPs products are normalized according to the BBPs species concentration maximum (at third day). 3D distribution and scale of normalized BBPs concentration are represented by greyscale legends. Black color in grey scale legends corresponds to maximum BBPs concentration (at third day). White color corresponds to zero BBPs concentration.

FIGS. 6-11 demonstrate that higher BBPs concentration close to larger cerebral arteries can be predictors of later development of cerebral vasospasm and formation of cerebral ischemia on that artery's smaller branches. In the presented example, the delayed ischemia was detected at the ninth day in the smaller branches coming from artery that contained several cerebral vasospasms 701, 702, 703 and 704.

FIGS. 7A, 7B, 7C, and 10 show that higher BBPs concentration on larger arteries is related to later appearance of several cerebral vasospasms 701, 702, 703, and 704. Higher BBPs concentration on smaller arteries is related to later formation of delayed cerebral ischemia on the artery branch of arteries with the spasms.

Figure 12:
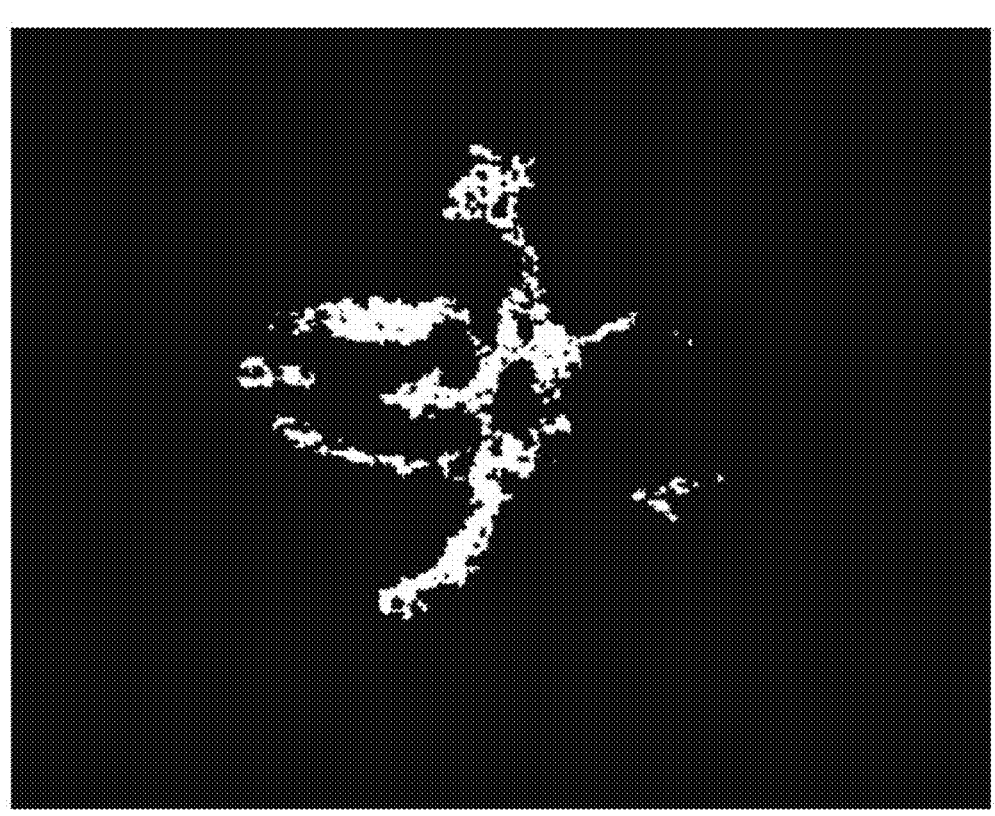
FIG. 12 is an example of applied segmentation mask for hemorrhage identification in CT images.

FIG. 12 is an example of an applied segmentation mask for hemorrhage identification in CT images. The segmentation mask is an array that is an output of the neural network and the algorithm to indicate the likelihood that the location corresponding to a pixel belongs to the hemorrhage. The figure is an example of a hemorrhage likelihood mask for one selected slice of a 3D CT image. Such a mask is identified for each slice of the 3D CT image and a set of all masks from each slice represents the 3D distribution of hemorrhage likelihood.

Figure 13:
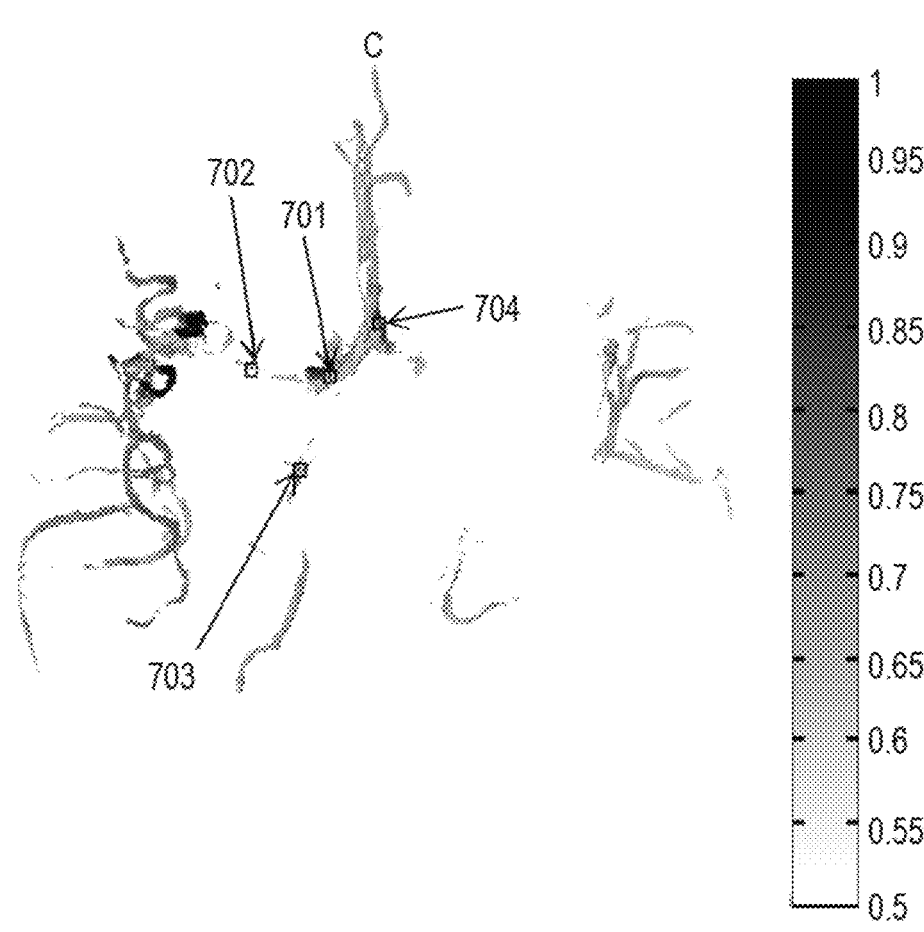
FIG. 13 is a calculated 3D map of cerebral vasospasm risk probability.
Figure 14:
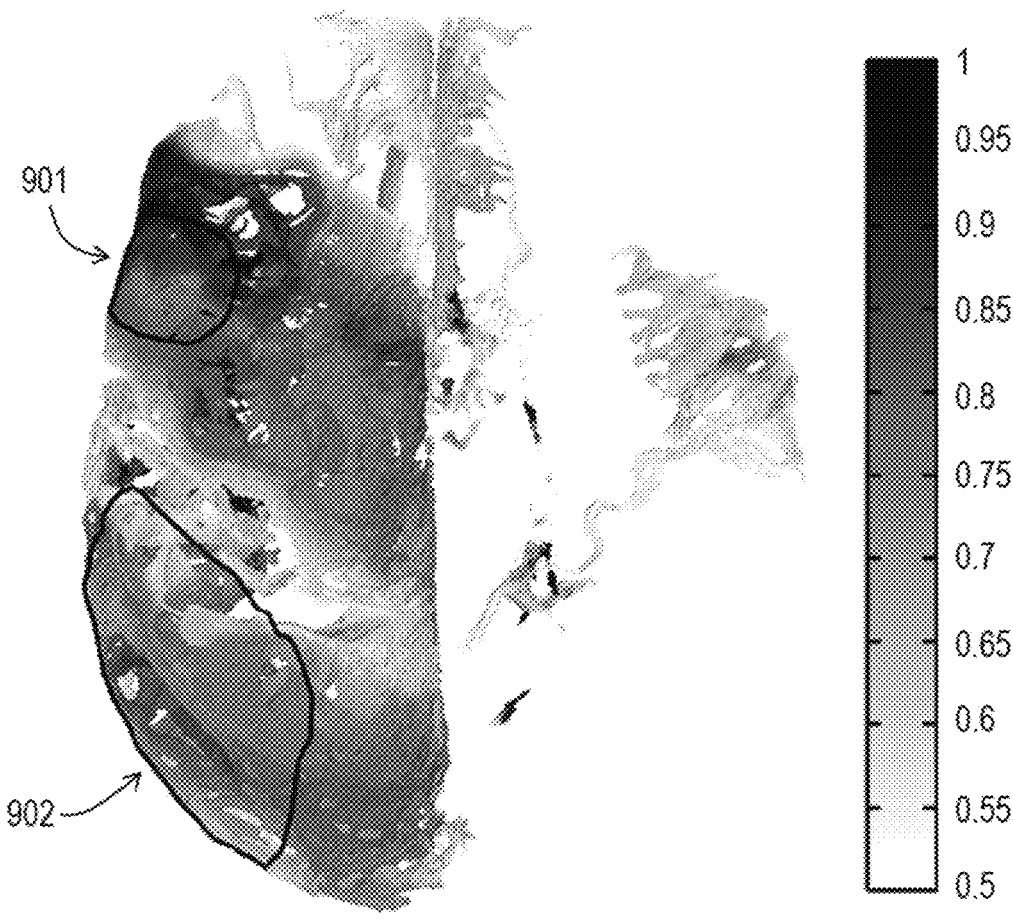
FIG. 14 is a calculated 3D map of delayed cerebral ishemia risk probability.

Example of risk prognostic information is provided in FIGS. 13 and 14. The 3D zones can be viewed by the operator to look for dark zones with risk factors above 0.5 in any specific brain zone which is associated with high risk of CV and DCI. The operator can visualize the 3D map of risk zones and manipulate them to view them at desired angles.

FIG. 13 is a 3D map of calculated cerebral vasospasm risk probability. The risk level is shown in grayscale legend. The grayscale corresponds to the cerebral vasospasm risk probability. The locations of actual cerebral vasospasms on the anterior artery are shown, 701, 702, and 704, as well as the location of an actual cerebral vasospasm on the posterior artery identified from the CT image on the 9th day.

FIG. 14 is a 3D map of calculated delayed cerebral ischemia risk probability. The black lines show the zones of actual ischemia 901 and 902, identified by a radiaologist from a CT image on the 9th day. The grayscale corresponds to the risk of delayed crebral ischemia probability.

Although specific advantages of the invention have been enumerated above, various embodiments may include some, none, or all of the enumerated advantages. Other technical advantages may become readily apparent to one of ordinary skill after review of the figures and description. Although exemplary embodiments are illustrated in the figures and described above, the principles of the present disclosure may be implemented using any number of techniques, whether currently known or not. The present disclosure should in no way be limited to the exemplary implementations and techniques illustrated in the drawings and described herein. It is understood that many modifications and variations may be devised to give the above description of the principles of the invention. It is intended that all such modifications and variations be considered as within the spirit and scope of this invention, as defined in the following claims.

What is claimed is:

1. An apparatus for predicting a cerebral vasospasm comprising;
   a CT scanner configured to take CT images of a patient;
   a computer system with a processor and a database of reference tomography images of segmented CT, CTA and MRI images;
   the processor is configured for conducting computational fluid dynamics calculations, for conducting automatic tomography image segmentation, to receive uploaded brain tomography images, and to extract 3D information of leaked blood, cerebral arteries and subarachnoid space;
   the processor is further configured to create a database of automated segmented images, process extracted 3D information on leaked blood, cerebral arteries and subarachnoid space (SAS) using computational fluid dynamics calculations to identify time-dependent wash out and spreading of leaked blood breakdown products (BBPs) within subarachnoid space, and to display to a user the results of the automatic tomography image segmentation with calculated 3D distribution of BBPs concentration on cerebral arteries walls and subarachnoid space locations.

2. The apparatus of claim 1 wherein the automatic tomography image segmentation includes a machine learning algorithm for the automatic segmentation of CT and CTA images.

3. The apparatus of claim 1 wherein the processor is configured to permit a user to manually alter the automatic tomography image segmentation.

4. The apparatus of claim 3 wherein the processor is configured to add manually altered automatic tomography image segmentations into the database of automated segmented images.

5. The apparatus of claim 1 wherein the processor is further configured to calculate a time-dependent spatial distribution of BBPs concentrations from the calculation of cerebrospinal fluid (CSF) flow and BBPs transport.

6. The apparatus of claim 5 wherein the processor is configured to use the calculated BBPs concentrations to locate zones with higher risk of cerebral vasospasm (CV) and delayed cerebral ischemia (DCI).

7. The apparatus of claim 6 wherein the processor is configured to use the distribution of BBPs concentration to provide a 3D map of CV and DCI probability.

8. The apparatus of claim 7 wherein the processor is configured to provide a 3D map of CV and DCI probability using the following equation:

$$P_{risk}(r_a, t) = F(c_i(r - r_a, t), D_a(r_a), C_a(r_a))$$

where
t represents time;
r represents a spatial position vector;

$r_a$ represents a spatial position vector pointing to a location on a cerebral arterial wall;

$P_{risk}(r_a, t)$ represents a time-dependent three-dimensional map of the probability of cerebral vasospasm and delayed cerebral ischemia;

$c_j(r-r_a, t)$ represents a time-dependent concentration of a blood breakdown product species at a spatial location offset from the cerebral arterial wall position $r_a$;

$D_a(r_a)$ represents a diameter of the cerebral artery at position $r_a$;

$C_a(r_a)$ represents a calcification level of the cerebral artery at position $r_a$;

F represents a function defining an integrative relationship between the probability of delayed cerebral ischemia and cerebral vasospasm at position $r_a$ and the parameters $c_j$, $D_a$, and $C_a$.

9. The apparatus of claim 1 wherein the processor is configured to issue a warning of cerebral vasospasm and delayed cerebral ischemia by determining risk zones with a high concentration of BBPs close to specific cerebral arteries at specific times.

10. The apparatus of claim 1 wherein the processor is configured to generate a segmentation mask which is an array that is an output of the neural network and the algorithm to indicate the likelihood that the location corresponding to a pixel belongs to the hemorrhage.

11. The apparatus of claim 1 wherein the process is configured to output an original CT scan of a patient and a pixel array of the same dimensions of the CT scan, each pixel in the pixel array has only values 0 or 1, where the value 1 of a pixel indicates the corresponding pixel of the CT scan is predicted to be hemorrhage location.

12. An apparatus for predicting a cerebral vasospasm comprising;
   a CT scanner configured to take CT images of a patient;
   a computer system with a processor and a database of reference tomography images of segmented CT, CTA and MRI images;
   the processor is configured for conducting computational fluid dynamics calculations, for conducting automatic tomography image segmentation, to receive uploaded brain tomography images, and to extract 3D information of leaked blood, cerebral arteries and subarachnoid space (SAS);
   the processor is further configured to process extracted 3D information on leaked blood, cerebral arteries and subarachnoid space using computational fluid dynamics calculations to identify time-dependent wash out and spreading of leaked blood breakdown products within subarachnoid space, and to display to a user the results of the automatic tomography image segmentation with calculated 3D distribution of blood breakdown product concentration on cerebral arteries walls and subarachnoid space locations.

13. A method for predicting a cerebral vasospasm comprising; acquiring CT, CTA and MRI images of leaked blood within the subarachnoid space (SAS) of a patient,
   extracting a 3D spatial distribution of leaked blood from within the SAS from CT and MRI images,
   calculating the volume of leaked blood using a manually segmented CT image,
   extracting from the CTA and MRI images a 3D distribution of main cerebral arteries,
   extracting a 3D image of the SAS from the MRI images,
   using a collection of segmented CT, CTA and MRI images to create a database used to train an automatic segmentation algorithm, using the automated segmentation algorithm to automatically segment CT and CTA images, calculating a generation of blood breakdown products (BBPs) from the spatial distribution of the leaked blood, calculating wash out and spreading of BBPs within the SAS by calculating the generation of BBPs in a leaked blood clot, BBPs diffusion and advection by cerebrospinal fluid (CSF) flow within the SAS, identifying critical zones of high concentrations of BBPs near arteries at specific times that are potential locations for cerebral vasospasm (CV) and delayed cerebral ischemia (DCI), and issuing a warning of a CV occurrence and DCI location and time in specific areas of the patient's cerebral vasculature where blood flow is maintained from identified vasospasmic artery.

14. The method of claim 13 further including calculating BBPs concentration within the SAS to identify ischemic zone locations.

15. The method of claim 14 further including using the distribution of BBPs concentration to provide a 3D map of CV and DCI probability.

16. The method of claim 15 further providing a 3D map of CV and DCI probability generated using the following equation:

$$P_{risk}(r_a, t) = F(c_i(r - r_a, t), D_a(r_a), C_a(r_a))$$

where t represents time;

r represents a spatial position vector;

$r_a$ represents a spatial position vector pointing to a location on a cerebral arterial wall;

$P_{risk}(r_a, t)$ represents a time-dependent three-dimensional map of the probability of cerebral vasospasm and delayed cerebral ischemia;

$c_i(r-r_a, t)$ represents a time-dependent concentration of a blood breakdown product species at a spatial location offset from the cerebral arterial wall position $r_a$;

$D_a(r_a)$ represents a diameter of the cerebral artery at position $r_a$;

$C_a(r_a)$ represents a calcification level of the cerebral artery at position $r_a$;

F represents a function defining an integrative relationship between the probability of delayed cerebral ischemia and cerebral vasospasm at position $r_a$ and the parameters $c_i$, $D_a$, and $C_a$.

* * * * *